US00PP25439P3

(12) United States Plant Patent
Roberts

(10) Patent No.: US PP25,439 P3
(45) Date of Patent: Apr. 14, 2015

(54) MINT PLANT 'STEENS MINT'

(50) Latin Name: ***Mentha* sp.**
Varietal Denomination: Steens Mint

(71) Applicant: Essex Laboratories, Inc., Napavine, WA (US)

(72) Inventor: Donald D. Roberts, Independence, OR (US)

(73) Assignee: Essex Laboratories, Inc., Napavine, WA (US)

( * ) Notice: Subject to any disclaimer, the term of this patent is extended or adjusted under 35 U.S.C. 154(b) by 138 days.

(21) Appl. No.: 13/815,159

(22) Filed: Feb. 4, 2013

(65) Prior Publication Data

US 2014/0223623 P1 Aug. 7, 2014

(51) Int. Cl.
*A01H 5/00* (2006.01)

(52) U.S. Cl.
USPC ..... Plt./259

(58) Field of Classification Search
USPC ..... Plt./259
See application file for complete search history.

(56) References Cited

U.S. PATENT DOCUMENTS

PP11,788 P2 2/2001 Roberts
PP13,720 P2 4/2003 Roberts

OTHER PUBLICATIONS

Gobert, V., "Hybridization in the section *Mentha* (Lamiaceae) inferred from AFLP markers," Am. J. Bot, Dec. 2002, 89 (12), pp. 2017-2023.
Fuchs, Sabine, et al., "Biosynthesis of Menthofuran in *Mentha×piperita;* Stereoselective and Mechanistic Studies"; J. Agric. Food Chem., 1999, 47 (10), pp. 4100-4105.
Dung, Jeremiah K.S., et al. Evaluation of *Verticillium* Wilt Resistance in *Mentha arvensis* and *M. longifolia* Genotypes, Plant Disease, Oct. 2010, vol. 94, pp. 1255-1260.
Rohloff, Jens, et al., Effect of Harvest Time and Drying Method on Biomass Production, Essential Oil Yield, and Quality of Peppermint (*Mentha piperita* L.); J. Agric. Food Chem., 2005, 53 (10), pp. 4143-4148.
Rohloff, Jens, Monoterpene Composition of Essential Oil from Peppermint (*Mentha piperita* L.) with Regard to Leaf Position Using Solid-Phase Microextraction and Gas Chromatography/Mass Spectrometry Analysis; J. Agric. Food Chem.; 1999, 47(9), pp. 3782-3786.

*Primary Examiner* — Annette Para
(74) *Attorney, Agent, or Firm* — Marger Johnson & McCollom, PC

(57) ABSTRACT

Mint selection 08-A20-3, denominated 'Steens Mint,' is a new *Mentha* sp. cultivar that produces a unique essential oil, has a compact plant type, produces more oil on a dry weight basis and has resistance to mint rust (*Puccinia methae*).

3 Drawing Sheets

Latin name of the genus and species: *Mentha* sp.
Variety denomination: 'STEENS MINT'.

FEDERAL SPONSORSHIP

None

TYPE OF PLANT AND NAME OF VARIETY

The present invention relates to a new and distinct variety of peppermint plant developed from a parent of the species *M. arvensis*. The new variety will be identified as 'Steens Mint.'

BACKGROUND OF THE INVENTION

This new mint was developed in a mint breeding program in which the primary objective was to develop a Mitcham type peppermint variety having a specific oil composition, acceptable yield and resistant to mint diseases. The new variety is as susceptible to mint wilt (soil borne fungus *Verticillium dahliae*) as its parent, but more resistant to mint rust (airborne fungus *Puccinia menthae*). 'Steens Mint' has a higher yield of oil than the control variety, 'Black Mitcham,' in test plots since 2009. This plant was selected from a population of mint seedlings in research plots on land near Monmouth, Oreg. and initially identified as 08-A20-3.

DISCOVERY AND ASEXUAL REPRODUCTION

'Steens Mint' originated as a seedling from 'Blanco,' an open pollinated commercial variety of *Mentha arvensis* included with other *M. arvensis* and male fertile *M. piperita* plants in a polycross breeding program. Diploid *M. piperita* is sterile and only becomes fertile in the polyploidy state. The parent plants in the polycross breeding system were composed of selected fertile male and female genotypes based on certain desirable characteristics.

'Steens Mint' is asexually propagated to maintain the cultivars genetic integrity and as a means of increasing the selection for commercial planting. Asexual propagation, by tip cuttings or stolon sections, is a common practice in commercial mint cultivation and serves as a means of propagating the normally sterile mint plant. The inventor has conducted asexual propagation with tip cuttings and stolon sections of 'Steens Mint' for greenhouse and field planting in Monmouth, Oreg., each year since 2008 and the genotype comes true to form with each generation.

SUMMARY OF THE INVENTION

Mint selection 08-A20-3, denominated 'Steens Mint,' is a new *Mentha* sp. cultivar that produces an essential oil different in composition than commercially grown mint varieties.

The essential oil is similar to standard mint oil in components composition but differs in the typical ratio of components. Organoleptically it differs from typical *Mentha piperita* peppermint oil. It is more resistant to mint rust than current commercially grown *Mentha arvensis* varieties.

BRIEF DESCRIPTION OF THE FIGURES

The accompanying color figures show typical, one year old, field grown vegetative growth of 'Steens Mint' and depicts the color as nearly as reasonably possible.

FIG. 1 illustrates the flowering pattern and multiple flowering shoots of my new mint plant in accordance with the present invention. FIG. 3 illustrates the flower spike with capitates flower development at the nodes of the spike.

FIGS. 2 and 3 illustrate the variance in leaf shape of my new mint plant depending on the location on plant. FIG. 2 illustrates the shape of the leaf collected at mid-plant and grown under a field environment, whereas, FIG. 3 illustrates the shape of leaf on a terminal flowering shoot.

DESCRIPTION OF PLANT

My new mint plant improves upon and is distinct from other mint plants in several characteristics, including but not limited to, the following:

1. The ability to produce an essential oil different in composition than typical commercial *M. arvensis*, but with similar components as 'Black Mitcham' peppermint (*M. piperita*);
2. Produce more oil on a dry weight basis than currently grown mint varieties;
3. A more compact plant but with a branching pattern similar to its parent;
4. An early spring growth similar to 'Black Mitcham' peppermint but with an earlier maturity for desirable chemical composition of its essential oil;
5. A level of resistance to mint rust equal to or greater than that of its *M. arvensis* female parent;

The essential oil extracted from 'Steens Mint' has a composition of components more like that of commercial oil produced by 'Black Mitcham' peppermint (*M. piperita*) than that of *M. arvensis* as illustrated in Table 1. However, the ratio of oil components in 'Steens Mint' is different from those of both *M. arvensis* and *M. piperita*. The concentration of menthone in oil of 'Steens Mint' is greater than that of *M. arvensis* and *M. piperita*. Menthofuran is present in the oil of 'Steens Mint' and absent in oil of its parent *M. arvensis*. Organoleptically, the oil of 'Steens Mint' is different from that of 'Black Mitcham' and *M. arvensis*, reflecting the difference in oil component ratios.

TABLE 1

A Comparison of 'Steens Mint' Oil collected from test plots near Monmouth, Oregon, to that of its *M. arvensis* parent, Commercial *M. arvensis*, and Commercial *M. piperita* Oils. 1/

| Essential Oil Components | *Mentha arvensis* Parent seedling 2/ | 'Steens Mint' Seedling 2/ | Commercial *M. arvensis* | Commercial *M. piperita* |
|---|---|---|---|---|
| 1-Limonene | 3.0 | 1.3 | 3.0 | 1.7 |
| 1,8-Cineole | <1.0 | <1.0 | <1.0 | 4.9 |
| 1-Menthone | 15.7 | 42.2 | 7.3 | 19.4 |
| Menthofuran | 0.0 | 3.8 | 0.0 | 4.2 |
| Isomenthone | 3.5 | 2.5 | 3.6 | 3.1 |
| 1-Menthyl Acetate | 3.7 | 4.3 | 2.9 | 5.3 |

TABLE 1-continued

A Comparison of 'Steens Mint' Oil collected from test plots near Monmouth, Oregon, to that of its *M. arvensis* parent, Commercial *M. arvensis*, and Commercial *M. piperita* Oils. 1/

| Essential Oil Components | *Mentha arvensis* Parent seedling 2/ | 'Steens Mint' Seedling 2/ | Commercial *M. arvensis* | Commercial *M. piperita* |
|---|---|---|---|---|
| 1-Menthol | 64.3 | 35.4 | 73.9 | 44.6 |
| Pulegone | <1.0 | <1.0 | 0.0 | 2.1 |

The numbers listed in the above table are percentages based upon the analysis of the respective mint oils by gas chromatography. The percentages are determined by calculation of the relative peak areas.
1/ Commercial oils of *M. arvensis* and *M. piperita* were samples of what is typically produced by mint growers.
2/ The essential oil of *M. arvensis* parent seedling and 'Steens Mint' were collected from plants growing in test plots in 2008.

TAXONOMIC DESCRIPTION OF 'STEENS MINT'

This new plant, under greenhouse and field growing conditions, is a bush type plant with lateral branches at each node of the main stems. The height of 'Steens Mint' is 75-90 cm and is equal to or greater than 'Black Mitcham' growing under similar conditions and will vary based on fertilizer, soil quality, and water application, amongst other known factors that affect growth patterns. Secondary and tertiary branching occurs to form a compact growth habit. When 'Steens Mint' is mature and ready for harvest, the main stem at mid-plant (approximately between the eleventh and twelfth node) is 4.7-5.7 mm in width. The secondary and tertiary branch stems are 2.0-3.1 mm and 1-2 mm in width, respectively. The average plant width is 28 cm and the average length of the main stem is 76 cm. The stems are square, glabrous, and a green color that matches Fifth Edition Royal Horticultural Society Colour Chart 143B green group.

Mature leaves at the bottom of the plant are ovate as are leaves on secondary branch stems. Leaves on upper mature plants, both main and secondary stems are more ovate lanceolate (FIG. 3). Mid-main stem leaf size at flowering is 25-30 mm in width and 35-50 mm in length. Leaf size on secondary branches at flowering is 17-20 mm in width and 25-32 mm in length. Leaf petioles on the main stem leaves are 8-10 mm in length while petioles on secondary branch stem leaves are 5-7 mm in length. Leaves on the mid-main and lower stem tend to be slightly lobed and irregular denticulate while the leaves on the upper plant tend to be more dentate. The main stem leaves have from 9 to 12 teeth on each side while the secondary branch leaves have 8-10 teeth on each side. The adaxial leaf surface is glabrous and is dark green in color, ranging from Fifth Edition Royal Horticultural Society Colour Chart 137B to 137C in the green group classification. The abaxial leaf surface is sub-glabrous with oil glands distributed across the surface and is light green in color as illustrated in The Fifth Edition Royal Horticultural Society Colour Chart 138A green group. The leaf has 6-9 lateral veins, more or less in parallel off the main vein that runs from the petiole to the tip of the leaf. The veins are prominent in all leaves of 'Steens Mint.'

The inflorescence is a conspicuous spike with capitate flowers developing at the nodes of the spike stem. The cylindrical spikes are about 30 mm in diameter and range from 200 to 250 mm in length. The capitate flowers are 15-20 mm in width and 10-15 mm in length. The flowers consist of five petals fused into a two lipped corolla. The corolla is light violet in color as illustrated in The Fifth Edition Royal Horticultural Society Colour Chart 84D in the Violet Group. The calyx is generally green and is 143C of Fifth Edition Royal Horticultural Society Colour Chart, Green Group. The gynoecium consists of a single pistil with two lobed stigma that is exserted. The androecium consists of four stamens, each with a distinct filament and anther.

While the plant that comprises the present invention has been describe in connection with a specific embodiment thereof, it will be understood that this application is intended to cover any variation, uses, or adaptation of the invention (particular those induced by cultivation under different environmental conditions) following, in general the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improving resistance to mint rust, and producing a unique essential oil.

* * * * *

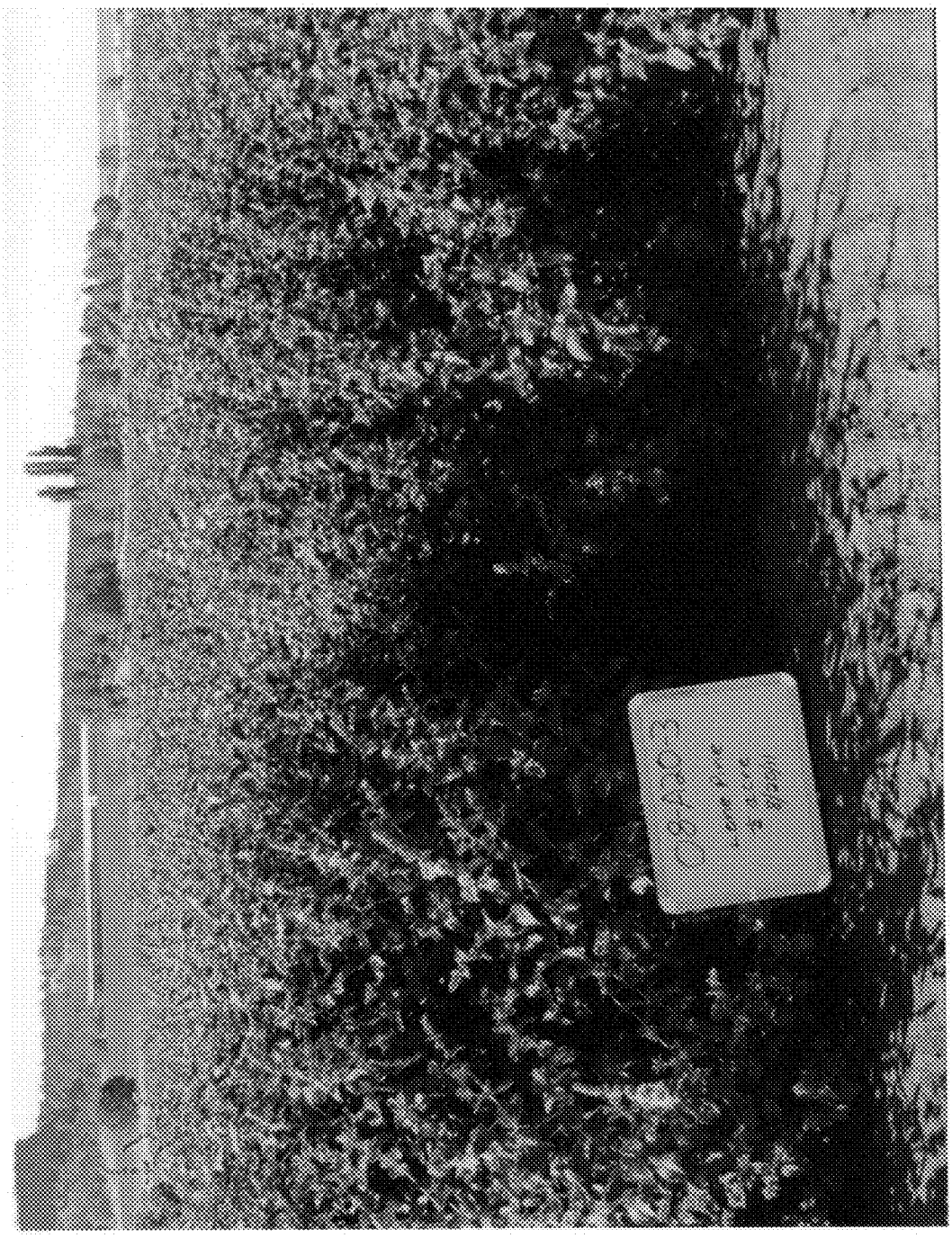

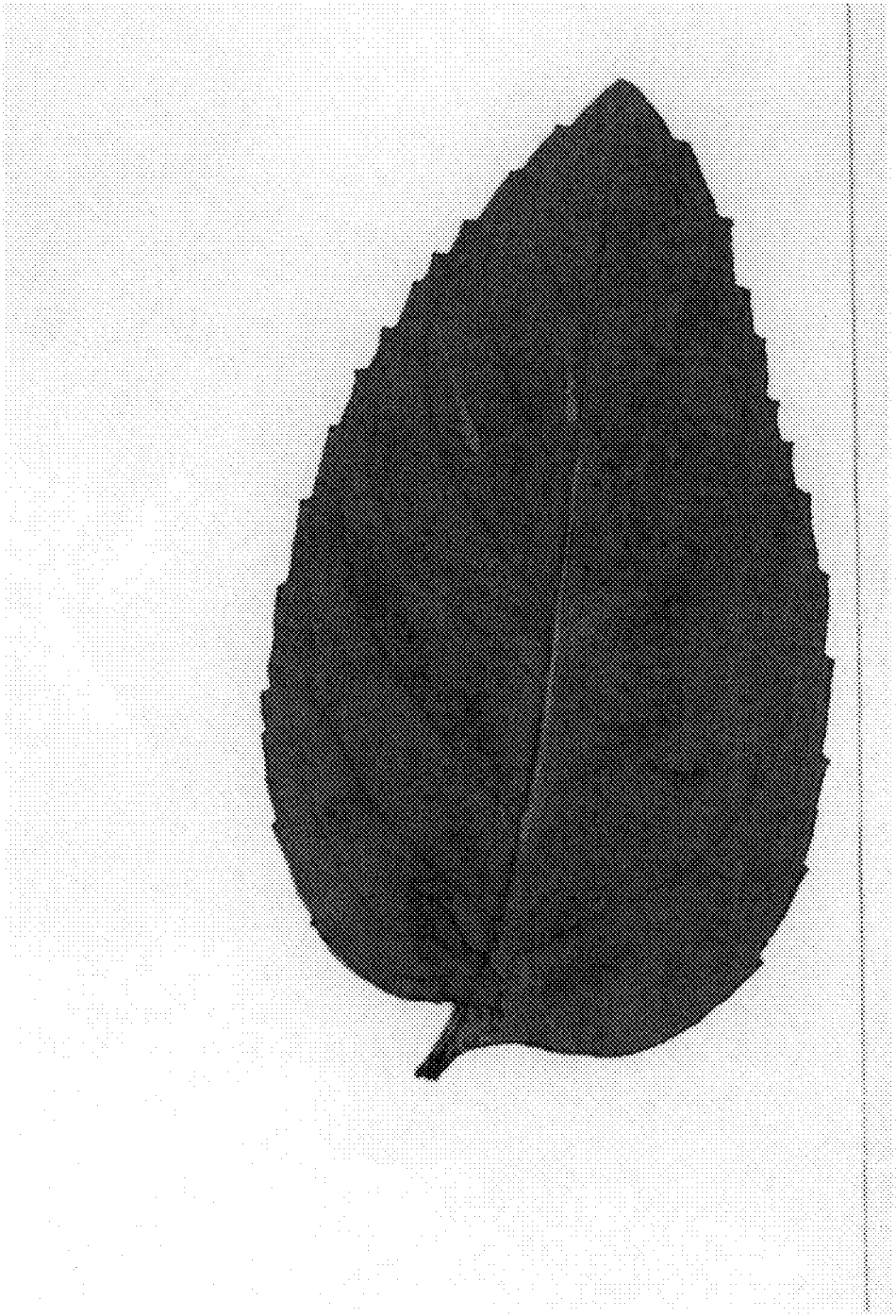
08-A20-3

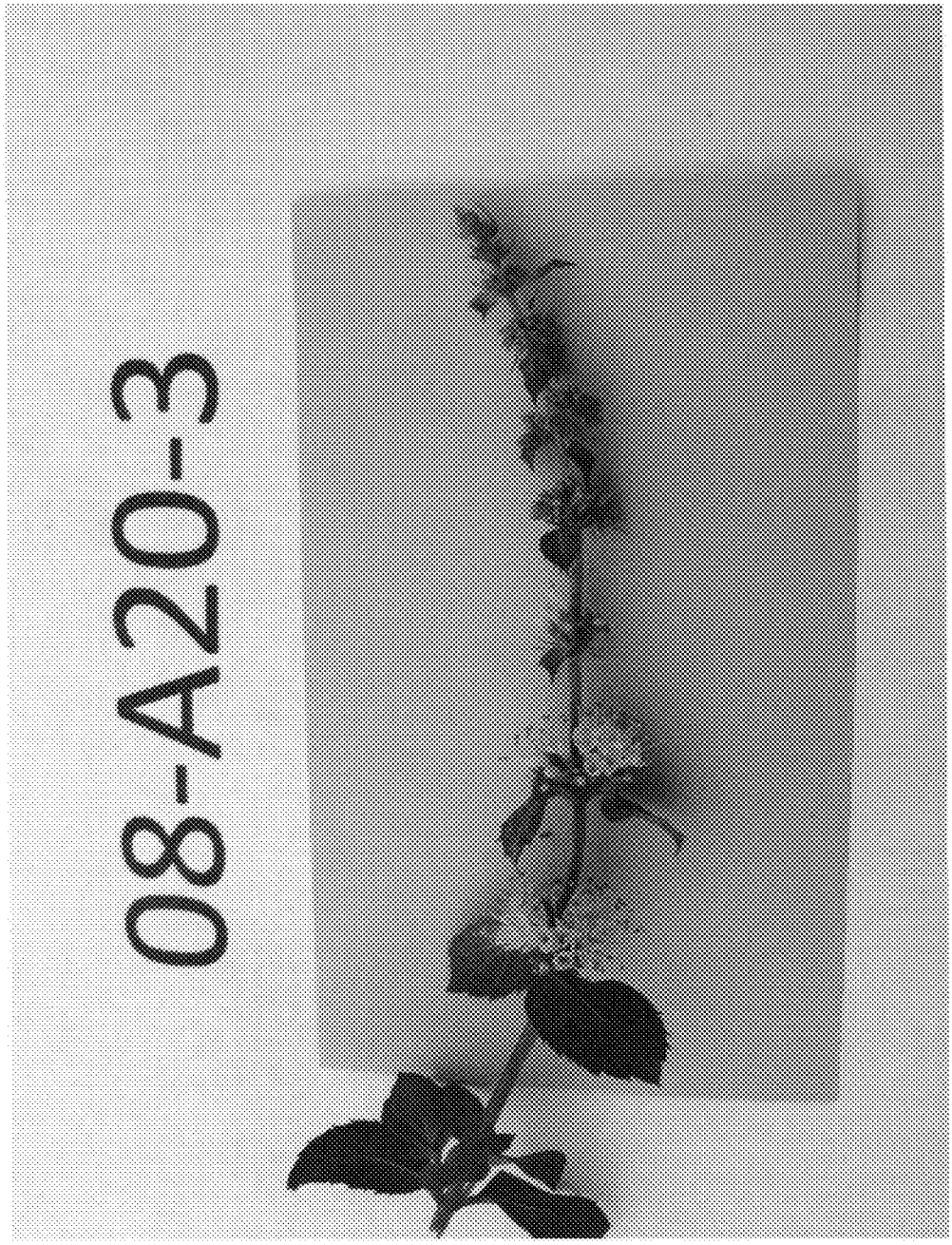
08-A20-3